United States Patent
Dumschat

(10) Patent No.: US 10,561,777 B2
(45) Date of Patent: Feb. 18, 2020

(54) DIALYSIS-CONCENTRATE PRODUCTION ASSEMBLY

(71) Applicant: INTERMEDT MEDIZIN & TECHNIK GMBH, Ostrhauderfehn (DE)

(72) Inventor: Christoph Dumschat, Leer (DE)

(73) Assignee: INTERMEDT MEDIZIN & TECHNIK GMBH, Ostrhauderfehn (DE)

(*) Notice: Subject to any disclaimer, the term of this patent is extended or adjusted under 35 U.S.C. 154(b) by 61 days.

(21) Appl. No.: 15/576,706

(22) PCT Filed: May 27, 2016

(86) PCT No.: PCT/EP2016/062083
§ 371 (c)(1),
(2) Date: Nov. 23, 2017

(87) PCT Pub. No.: WO2016/189161
PCT Pub. Date: Dec. 1, 2016

(65) Prior Publication Data
US 2018/0133386 A1    May 17, 2018

(30) Foreign Application Priority Data

May 27, 2015 (DE) .................. 20 2015 102 734 U

(51) Int. Cl.
*A61M 1/16* (2006.01)
*A61M 39/10* (2006.01)
(52) U.S. Cl.
CPC ........ *A61M 1/1666* (2014.02); *A61M 1/1668* (2014.02); *A61M 39/10* (2013.01);
(Continued)

(58) Field of Classification Search
CPC .................................................. A61M 1/1666
(Continued)

(56) References Cited

U.S. PATENT DOCUMENTS 70,414 A * 11/1867 Cook ..................... B65D 25/16
217/3 CB
183,010 A * 10/1876 Knapp ................... B65D 7/045
220/661
(Continued)

FOREIGN PATENT DOCUMENTS

DE        103 13 965 B3    10/2004
EA           017416 B1     12/2012
WO   WO 2012/066482 A1     5/2012

*Primary Examiner* — David L Sorkin
(74) *Attorney, Agent, or Firm* — Norman B. Thot

(57) ABSTRACT

A dialysis concentrate production assembly for producing a dialysis concentrate liquid by dissolving a dry concentrate in water. The dialysis concentrate production assembly includes a mobile interchangeable container which contains the dry concentrate and a stationary production system. The mobile interchangeable container includes an outlet port and a combined port. The stationary production system is fluidically connected to the outlet port and to the combined port via coupling assemblies via which the dry concentrate is mixed with the water to form the liquid dialysis concentrate. At least one coupling assembly includes a system-side coupling body with a liquid line connector having a non-circular cross-section, and a container-side coupling body with a liquid line socket having a non-circular cross-section which is complementary to the non-circular cross section of the liquid line connector. The liquid line connector and the liquid line socket can be plugged together in only one single rotational position.

12 Claims, 4 Drawing Sheets

(52) U.S. Cl.
CPC ... *A61M 39/105* (2013.01); *A61M 2039/1033* (2013.01); *A61M 2039/1094* (2013.01); *A61M 2205/27* (2013.01); *A61M 2205/3331* (2013.01); *A61M 2205/6045* (2013.01); *A61M 2205/6054* (2013.01)

(58) Field of Classification Search
USPC ........................................................ 285/914
See application file for complete search history.

(56) References Cited

U.S. PATENT DOCUMENTS

| | | | | |
|---|---|---|---|---|
| 3,159,306 | A * | 12/1964 | Lyall | E03B 11/00 220/245 |
| 3,293,860 | A * | 12/1966 | Stedfeld | B29C 53/602 156/155 |
| 3,940,013 | A * | 2/1976 | Bonnett | B65D 1/16 220/751 |
| 4,150,673 | A * | 4/1979 | Watt | A61J 1/10 128/DIG. 24 |
| 7,484,769 | B2 * | 2/2009 | Domash | A61M 39/10 285/124.4 |
| 2003/0168120 | A1 | 9/2003 | Brehm et al. | |
| 2004/0217586 | A1 * | 11/2004 | Mastropaolo | F16L 35/00 285/124.1 |
| 2011/0144626 | A1 | 6/2011 | Hall | |
| 2014/0056781 | A1 | 2/2014 | Jaaskelainen et al. | |
| 2014/0191501 | A1 | 7/2014 | Brugger et al. | |
| 2014/0309584 | A1 | 10/2014 | Bluchel et al. | |
| 2015/0083647 | A1 | 3/2015 | Meyer et al. | |

* cited by examiner

DIALYSIS-CONCENTRATE PRODUCTION ASSEMBLY

CROSS REFERENCE TO PRIOR APPLICATIONS

This application is a U.S. National Phase application under 35 U.S.C. § 371 of International Application No. PCT/EP2016/062083, filed on May 27, 2016 and which claims benefit to German Patent Application No. 20 2015 102 734.6, filed on May 27, 2015. The International Application was published in German on Dec. 1, 2016 as WO 2016/189161 A1 under PCT Article 21(2).

FIELD

The present invention relates to a dialysis concentrate production assembly for the production of a dialysis concentrate liquid by dissolving a dry concentrate in water.

BACKGROUND

For performing a typical dialysis treatment, 150 to 200 l of dialysis fluid are usually required. The dialysis liquid is generally produced in the dialysis apparatus from two dialysis concentrate fluids and water which are mixed in a ratio of, for example, 1/35. For the production of the dialysis liquid itself, an alkaline dialysis concentrate liquid, which is usually a sodium hydrogen carbonate solution of a defined concentration, and an acidic dialysis concentrate liquid, which contains all the other components necessary for the dialysis liquid in the required concentration, are mixed homogeneously with water.

DE 103 13 965 B3 describes a dialysis concentrate production assembly where a dry concentrate is mixed homogeneously with water to produce the dialysis concentrate liquid. The dry concentrate is supplied in a mobile and reusable exchangeable container having two liquid ports, i.e., a combined port that can be used in both directions, and an outlet port through which liquid can be discharged from the exchangeable container. The two ports are connected to a stationary production system at the point of use. By pumping and directing water in a corresponding manner, the dry concentrate is thereafter dissolved in water and mixed homogeneously to obtain the dialysis concentrate liquid. The liquid is pumped into the exchangeable container under a certain pressure and flows from the outlet port under pressure.

The fluidic connection of the production system to the two ports is respectively made by a coupling assembly which has no special features so that a risk of erroneous operation and leaks fundamentally exists.

SUMMARY

An aspect of the present invention is to provide a dialysis concentrate production assembly having operationally safe coupling assemblies with good sealing properties. Another aspect of the present invention is to provide an interchangeable container for a dialysis concentrate production assembly which can be connected to the production system in an operationally safe manner and with high fluidic tightness.

In an embodiment, the present invention provides a dialysis concentrate production assembly for producing a dialysis concentrate liquid by dissolving a dry concentrate in water. The dialysis concentrate production assembly includes a mobile interchangeable container configured to contain the dry concentrate and a stationary production system. The mobile interchangeable container comprises an outlet port and a combined port. The stationary production system is fluidically connected to the outlet port and to the combined port via at least two coupling assemblies via which the dry concentrate is mixed with the water so as to form the liquid dialysis concentrate. At least one of the at least two coupling assemblies comprises a system-side coupling body which comprises a liquid line connector having a non-circular cross-section, and a container-side coupling body which comprises a liquid line socket having a non-circular cross-section which is complementary to the non-circular cross section of the liquid line connector. The liquid line connector and the liquid line socket are configured so as to be plugged together in only one single rotational position.

BRIEF DESCRIPTION OF THE DRAWINGS

The present invention is described in greater detail below on the basis of embodiments and of the drawings in which.

DETAILED DESCRIPTION

Figure 1:
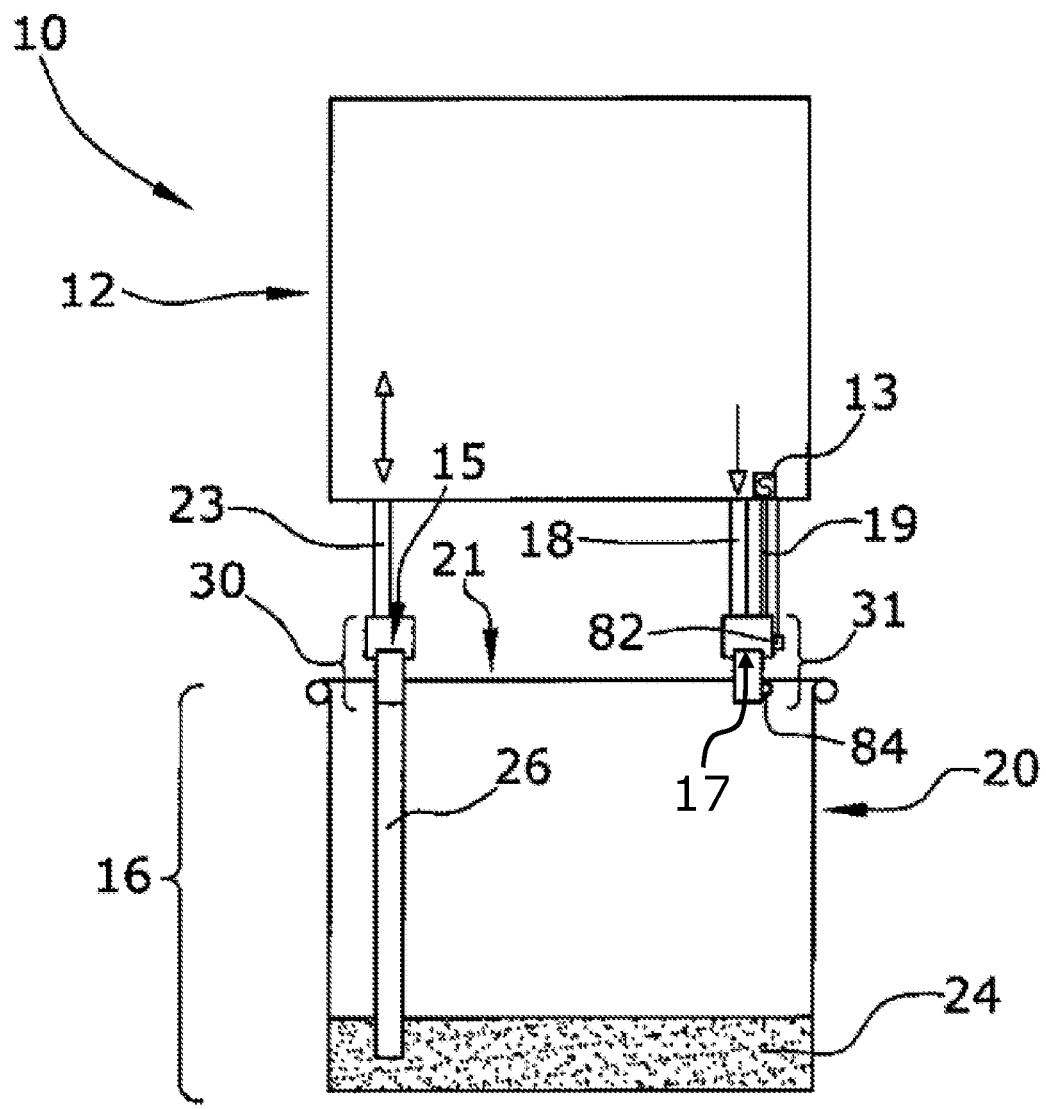
FIG. 1 shows a schematic illustration of a production assembly for the production of a dialysis concentrate liquid comprising a stationary production system and an interchangeable container.
Figure 2:
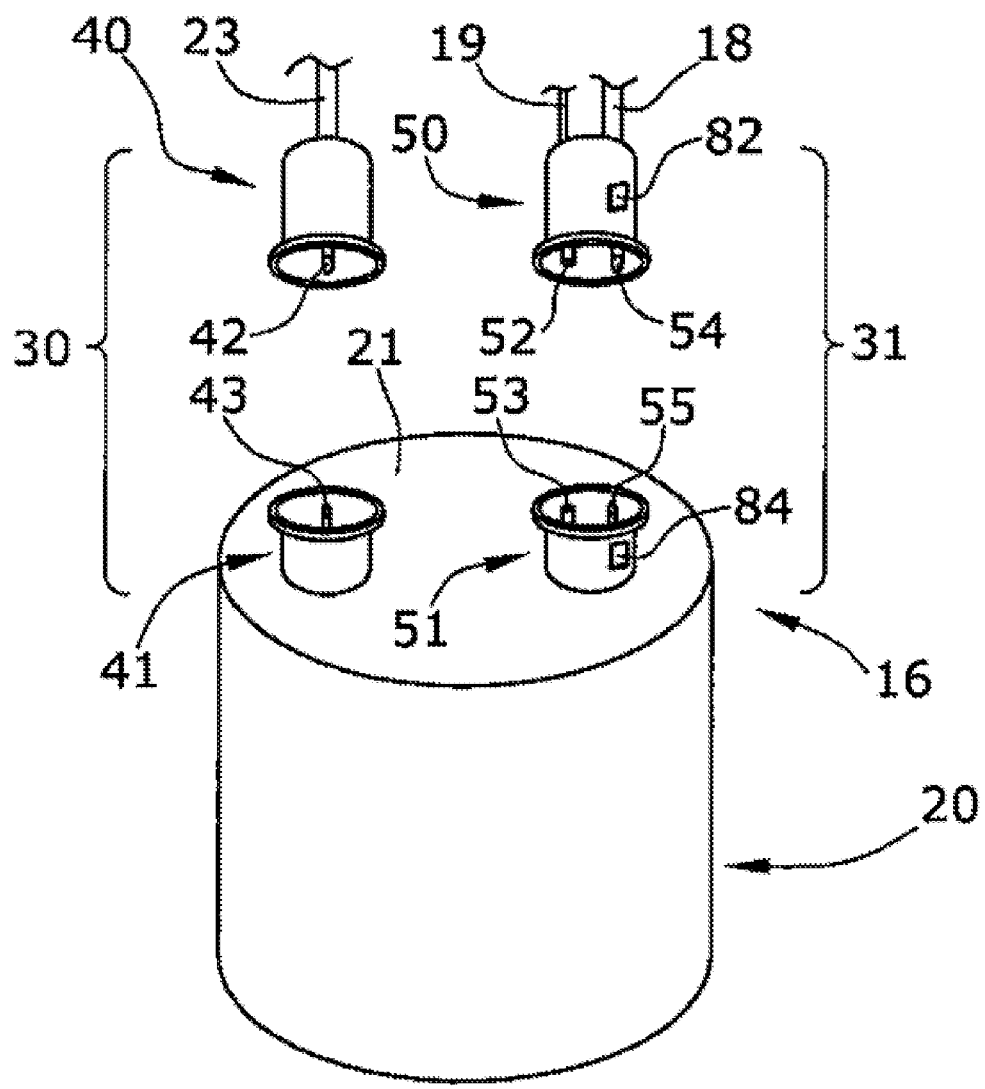
FIG. 2 shows the coupling bodies of the coupling assemblies for the fluidic connection of the interchangeable container to the production system of FIG. 1.

The interchangeable container of the present invention, which stores the dry concentrate, has an outlet port and a combined port. The two ports are each fluidically connected to the stationary production system by one respective coupling assembly. Each coupling assembly has a system-side coupling body and a container-side coupling body. The coupling bodies are complex structures that make both the mechanic and the fluidic connection. The container-side coupling body has a liquid line connector of non-circular cross section which corresponds to and is plugged into a corresponding and complementary liquid line socket of non-circular cross section provided at the system-side coupling body. The liquid line connector and the liquid line socket are shaped so that they can be plugged into each other in only one rotational position. The liquid line connector may alternatively also be provided at the container-side coupling body, and the liquid line socket may be provided at the system-side coupling body. The line socket and the line connector of the outlet port coupling assembly can, for example, be shaped differently from the line socket and the line connector of the combined port coupling assembly. This not only provides that the coupling assembly is plugged together in a manner safe to operate and to handle, but also excludes an inversion of the connections for the outlet port and the combined port.

By defining a single rotational position for plugging the line socket and the line connector together, it is possible to exclude a turning of the line socket and the line connector relative to each other prior and during plugging, during operation, or during the uncoupling of the respective coupling assembly. The stress on gaskets, sealing rings etc. is thereby significantly reduced, whereby fluidic tightness is also provided in case of multiple use of the interchangeable container. In an embodiment, the liquid line connector and the liquid line socket can, for example, each have an oval shape. Tight radii are thereby in particular avoided with respect to the cross-sectional shape of the line connector and the line socket so that a reliable fluid-tight sealing of the coupling assembly can be provided even under pressure, while at the same time realizing a non-circular cross-sectional shape that allows the line socket and the line connector to be plugged together in only a single rotational position.

In an embodiment, the production system can, for example, comprise a fluidic pressure sensor which is fluidically connected to one of the two coupling assemblies via a line having a system-side pressure sensor line connector and a corresponding container-side pressure sensor line socket. The line socket may alternatively also be provided on the side of the system, and the line connector may be provided on the side of the container. The respective coupling body thus has two line connectors or line sockets, i.e., a line connector for the liquid and a pneumatic line connector. Using the pneumatic connection from the interior of the interchangeable container to the pressure sensor of the production system makes it possible to constantly monitor the internal pressure in the interchangeable container during the mixing operation so that the internal pressure in the interchangeable container can be set and controlled in an optimal manner by controlling corresponding liquid pumps in the production system. It is thus possible to provide a certain mixing intensity and to in particular set a relatively low overpressure in the interchangeable container so that leaks or damages due to overpressure can be avoided.

In an embodiment, the liquid line connector can, for example, have an annular groove on its outer side, elongated in the axial direction, in which a flexible O-ring is seated. The annular groove has an axial length that is at least 1.5 times, for example, at least 2.0 times the diameter of the body of the O-ring. The radial inner side of the O-ring thus abuts on the bottom of the annular groove. Upon insertion of the liquid line connector into the corresponding liquid line socket, the radial outer side of the O-ring contacts a cylindrical sealing section of the line socket so that, upon further plugging, the O-ring is rolled between the two cylindrical surfaces of the annular groove and the line socket at approximately half the speed of the axial plugging movement. The friction at the O-ring is thereby minimized both when the relevant coupling assembly is plugged together and when it is detached so that the mechanical wear at the O-ring is minimized and plugging and unplugging only requires little plugging force due to the low friction.

In an embodiment, the coupling bodies of the coupling assembly can, for example, be made of a plastic material, for example, of a plastic material without fiber reinforcement. The coupling bodies are not made of metal which might be corrosive with regard to the chlorides and acids contained in the dialysate concentrate liquid or which must be protected therefrom in a complex manner.

In an embodiment, the container-side coupling body can, for example, have an RFID identification transmitter and the system-side coupling body can, for example, have an RFID receiver for reading an identification from the RFID identification transmitter. The identification stored in the identification transmitter can, for example, identify the interchangeable container and/or the dry concentrate stored in the interchangeable container. The stationary production system can be retrieved from the identification transmitter via the RFID receiver when plugging the relevant coupling assemblies together. It is thereby possible, for example, to provide that the expiry date of the relevant dry concentrate has not yet expired. The identification may also store content information about the dry concentrate. Finally, the identification may also be used to store indications about the origin, the age, and the number of re-uses of the interchangeable container.

In an embodiment, the liquid line connector and/or the corresponding liquid line socket can, for example, be provided with a circular chamfer in the opening region which facilitates the insertion and the plugging together of the line socket and the line connector.

In an embodiment, the coupling assembly can, for example, have a bayonet assembly by which a bayonet lock is realized. The coupling assembly can in particular have a swivel nut at one of the two coupling bodies, which nut comprises one side of the bayonet assembly. The bayonet assembly has a small locking angle of less than 70° so that the rotational closing movement of the swivel nut is at most 70°. The bayonet assembly further has an undercut axial slope so that the swivel nut is axially braced during the locking movement. The swivel nut further comprises a plurality of radial locking noses with radial slopes which realize a centering of the swivel nut and the coupling body connected thereto.

The swivel nut can, for example, have rotary end stops which limit the rotational locking movement.

In an embodiment, the interchangeable container can, for example, have a riser adjoining the combined port, the riser protruding downward at least into the lower third of the interchangeable container. The riser is oval in shape similar to the line socket via which the riser is or is to be connected to the relevant line connector. The riser body also forms the line socket.

An embodiment of the present invention will be explained below under reference to the drawings.

FIG. 1 schematically illustrates a dialysis concentrate production assembly 10 for the production of a dialysis concentrate liquid by dissolving a dry concentrate 24 in water. The production assembly 10 comprises a mobile interchangeable container 16 holding the dry concentrate 24 and a stationary production system 12 comprising a plurality of components, in particular valves, pumps, and a system control.

The mobile interchangeable container 16 has a barrel-like container body 20 whose top is closed fluid-tightly by a container cover 21. At the container cover 21, the mobile interchangeable container 16 has two liquid ports, namely, a combined port 15 and an outlet port 17. The combined port 15 of the mobile interchangeable container 16 is in fluid communication with the production system 12 via a combined port coupling assembly 30 and a liquid line 23. The outlet port 17 is also in fluid communication with the production system 12 via an outlet port coupling assembly 31 and a liquid assembly 18. The outlet port coupling assembly 31 is further pneumatically connected to a pressure sensor 13 of the production system 12 via a pneumatic pressure line 19. An RFID receiver 82 of the outlet port coupling assembly 31 is electronically connected to the production system 12 via a data line.

The mobile interchangeable container 16 comprises a riser 26 of oval cross section which is connected to or opens into the combined port 15. The body of the riser 26 forms the riser 26 and a container-side line socket.

Figure 3:
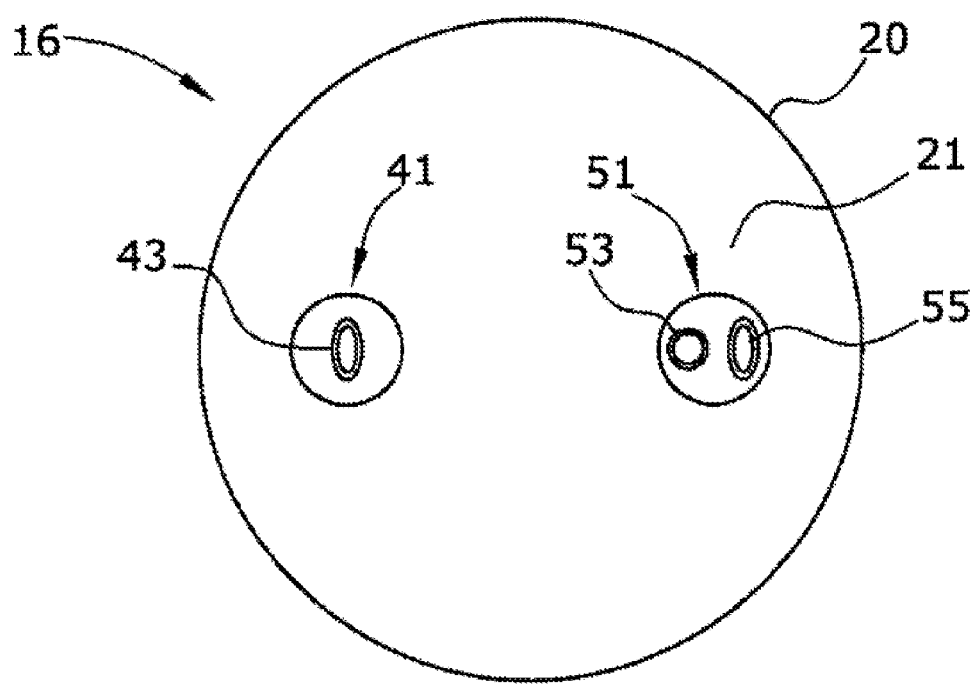
FIG. 3 shows a top plan view on the container cover of the interchangeable container in FIG. 1.

FIG. 3 illustrates the two coupling assemblies 30, 31 is a state not plugged into each other. The combined port coupling assembly 30 is illustrated on the left, the combined port coupling assembly 30 being formed by two coupling bodies 40, 41, namely, a system-side coupling body 40 with a line connector 42 of oval cross section and a container-side coupling body 41 with a line socket 43 also of oval cross section. The coupling bodies 40, 41, the line connector 42, and the line socket 43 are designed and arranged so that the two coupling bodies 40, 41 can be plugged axially, i.e., in the plugging direction, into each other in only one rotational position. This may be realized, for example, by the fact that the oval line connector 42 or the corresponding oval line socket 43 are not arranged centrically in the cylindrical housing of the respective coupling body 40, 41.

The outlet port coupling assembly 31 has a system-side coupling body 50 and a container-side coupling body 51. The container-side coupling body 51 has a liquid line socket 55 in the cylindrical coupling housing, which liquid line socket 55 corresponds to a corresponding liquid line connector 54 of the system-side coupling body 50. The liquid line connector 54 and the liquid line socket 55 are oval in cross section and are arranged eccentrically in the respective coupling body.

The outlet port coupling assembly 31 further has a pressure sensor line connector 52 at the system-side coupling body 50 and a corresponding pressure sensor line socket 53 at the container-side coupling body 51. A pneumatic connection is thereby made from the interior of the mobile interchangeable container 16 to the system-side pressure sensor 13.

An RFID identification transmitter 84 is fixed on the outer side of the container-side coupling body 51. On the system-side coupling body 50, an RFID receiver 82 is arranged that can read the identification or identification data from the identification transmitter 84 when the coupling bodies 50, 51 are plugged together. The RFID identification transmitter 84 in particular stores a unique identification of the mobile interchangeable container 16, information about the shelf life, the composition of the dry concentrate 24, as well as shelf life information regarding the mobile interchangeable container 16.

Figure 4:
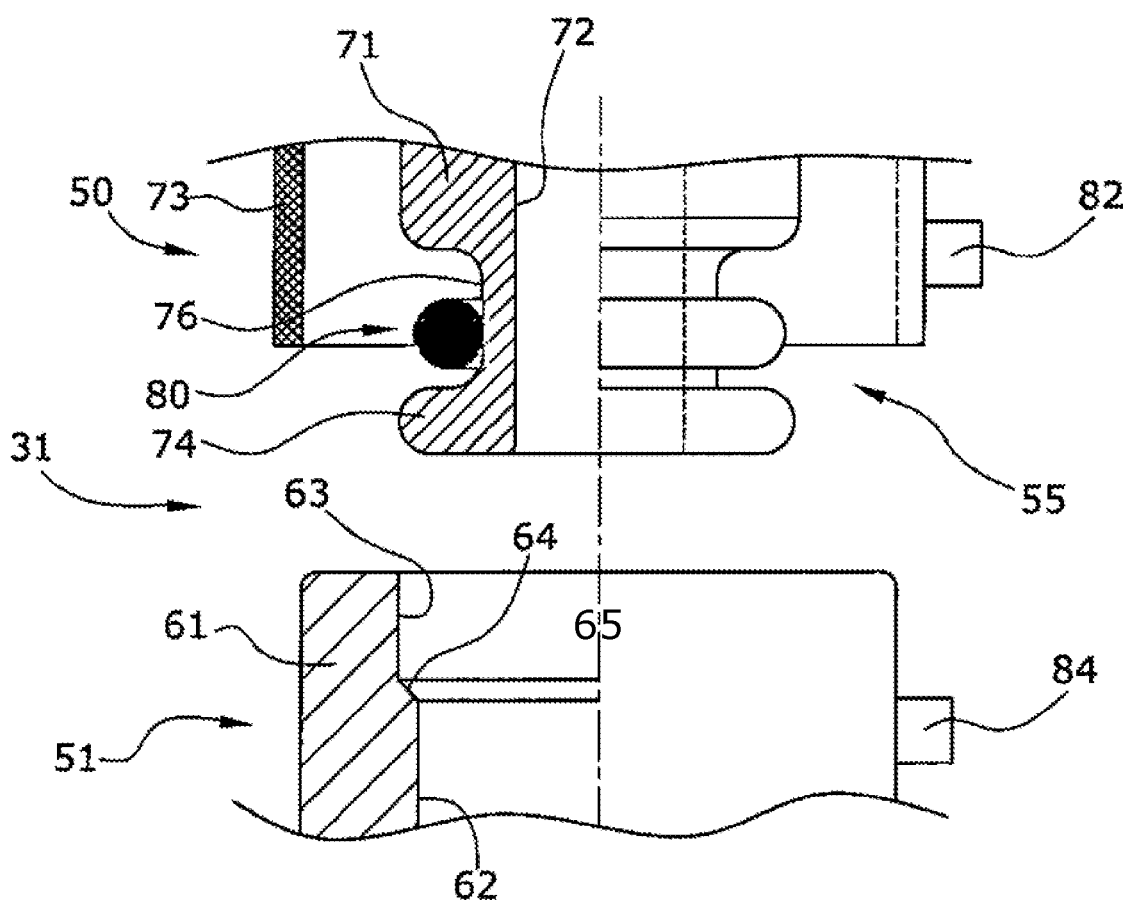
FIG. 4 shows a longitudinal section of the coupling bodies of the outlet port coupling assembly of the production assembly in FIG. 1.

FIG. 4 illustrates the two coupling bodies 50, 51 of the outlet port coupling assembly 31 in partial longitudinal section. The system-side coupling body 50 has a cylindrical coupling housing 73 in which the liquid line socket 55 is arranged non-centrically, liquid line socket 55 being formed by a substantially cylindrical plug body 71 with a substantially cylindrical inner side 72 and a substantially cylindrical outer side. The plug body 71 has an annular groove 76 at the end of the outer side in which an O-ring 80 is seated so that the O-ring 80 can be rolled, the annular groove 76 being elongated in the plugging direction or in the axial direction. At the end, the annular groove 76 is delimited by a corresponding annular bead 74 of the plug body 71. The axial length of the annular groove 76 is about three times the diameter of the O-ring 80 so that the O-ring 80 can roll therein completely approximately once.

The corresponding container-side coupling body 51 of the mobile interchangeable container 16 has a substantially cylindrical socket body 61 whose outer diameter is slightly smaller than the inner diameter of the system-side cylindrical plug housing 73. At the open side, the socket body 61 has a plug-in bore 65 into which the plug body 71 can be plugged, the O-ring 80 being slightly compressed and at the same time rolled between the bottom wall of the annular groove 76 and the cylindrical inner wall 63 of the socket body 61. The socket body 61 has a step 64 on the inner side via which the inner circumference tapers to a bore 62 with a smaller inner diameter.

The coupling bodies 40, 50, 41, 51 of the coupling assemblies 30, 31 are entirely made of a plastic material.

The present invention is not limited to embodiments described herein; reference should be had to the appended claims.

What is claimed is:

1. A dialysis concentrate production assembly for producing a dialysis concentrate liquid by dissolving a dry concentrate in water, the dialysis concentrate production assembly comprising:
   a mobile interchangeable container configured to contain the dry concentrate, the mobile interchangeable container comprising an outlet port and a combined port; and
   a stationary production system which is fluidically connected to the outlet port and to the combined port via at least two coupling assemblies via which the dry concentrate is mixed with the water so as to form the liquid dialysis concentrate,
   wherein,
   at least one of the at least two coupling assemblies comprises a system-side coupling body which comprises a liquid line connector having a non-circular cross-section, and a container-side coupling body which comprises a liquid line socket having a non-circular cross-section which is complementary to the non-circular cross section of the liquid line connector,
   the liquid line connector and the liquid line socket are configured so as to be plugged together in only one single rotational position,
   one of the at least two coupling assemblies is a coupling assembly comprising a system-side pressure sensor line connector and a container-side pressure sensor line socket which corresponds to the system-side pressure sensor line connector, and
   the stationary production system comprises a pressure sensor which is in a fluidic communication with the coupling assembly.

2. The dialysis concentrate production assembly as recited in claim 1, wherein the liquid line connector and the liquid line socket each have an oval shape.

3. The dialysis concentrate production assembly as recited in claim 2, wherein the mobile interchangeable container further comprises an oval riser.

4. The dialysis concentrate production assembly as recited in claim 1, wherein,
   the liquid line connector comprises an annular groove on an outer side in which a flexible O-ring is seated, and
   the annular groove comprises an axial length which is at least 1.5 times a diameter of the O-ring so that the O-ring can roll axially in the annular groove when the liquid line connector is plugged into the liquid line socket.

5. The dialysis concentrate production assembly as recited in claim 1, wherein each of the system-side coupling body and the container-side coupling body is made of a plastic material.

6. The dialysis concentrate production assembly as recited in claim 1, wherein,
   the container-side coupling body further comprises an RFID identification transmitter which comprises an identification, and
   the system-side coupling body further comprises an RFID receiver which is configured to read the identification from the RFID identification transmitter.

7. A dialysis concentrate production assembly for producing a dialysis concentrate liquid by dissolving a dry concentrate in water, the dialysis concentrate production assembly comprising:
- a mobile interchangeable container configured to contain the dry concentrate, the mobile interchangeable container comprising an outlet port and a combined port; and
- a stationary production system which is fluidically connected to the outlet port and to the combined port via at least two coupling assemblies via which the dry concentrate is mixed with the water so as to form the liquid dialysis concentrate, wherein,
- at least one of the at least two coupling assemblies comprises a system-side coupling body which comprises a liquid line connector having a non-circular cross-section, and a container-side coupling body which comprises a liquid line socket having a non-circular cross-section which is complementary to the non-circular cross section of the liquid line connector,
- the liquid line connector and the liquid line socket are configured so as to be plugged together in only one single rotational position,
- the liquid line connector comprises an annular groove on an outer side in which a flexible O-ring is seated, and
- the annular groove comprises an axial length which is at least 1.5 times a diameter of the O-ring so that the O-ring can roll axially in the annular groove when the liquid line connector is plugged into the liquid line socket.

8. The dialysis concentrate production assembly as recited in claim 7, wherein the liquid line connector and the liquid line socket each have an oval shape.

9. The dialysis concentrate production assembly as recited in claim 8, wherein the mobile interchangeable container further comprises an oval riser.

10. The dialysis concentrate production assembly as recited in claim 7, wherein,
- one of the at least two coupling assemblies is a coupling assembly comprising a system-side pressure sensor line connector and a container-side pressure sensor line socket which corresponds to the system-side pressure sensor line connector, and
- the stationary production system comprises a pressure sensor which is in a fluidic communication with the coupling assembly.

11. The dialysis concentrate production assembly as recited in claim 7, wherein each of the system-side coupling body and the container-side coupling body is made of a plastic material.

12. The dialysis concentrate production assembly as recited in claim 7, wherein,
- the container-side coupling body further comprises an RFID identification transmitter which comprises an identification, and
- the system-side coupling body further comprises an RFID receiver which is configured to read the identification from the RFID identification transmitter.

* * * * *